US00PP20346P2

(12) United States Plant Patent
Jury

(10) Patent No.: US PP20,346 P2
(45) Date of Patent: Sep. 22, 2009

(54) ***MAGNOLIA* PLANT NAMED 'JURMAG4'**

(50) Latin Name: *Magnolia hybrida*
Varietal Denomination: JURmag4

(76) Inventor: Mark Jury, 589 Otaraoa Road R.D. 43, Waitara, North Taranaki (NZ)

( * ) Notice: Subject to any disclaimer, the term of this patent is extended or adjusted under 35 U.S.C. 154(b) by 0 days.

(21) Appl. No.: 12/148,330

(22) Filed: Apr. 18, 2008

(30) Foreign Application Priority Data

Apr. 1, 2008 (NZ) ..... SHM240

(51) Int. Cl.
*A01H 5/00* (2006.01)

(52) U.S. Cl. ..... Plt./223
(58) Field of Classification Search ..... Plt./223
See application file for complete search history.

*Primary Examiner*—Susan B McCormick Ewoldt

(57) ABSTRACT

A new and distinct *Magnolia* cultivar named 'JURmag4' is disclosed, characterized by having an upright, fastigiate habit., dark pink petals, controlled growth without pruning, star shaped flowers and profuse flowering. The new variety is a *Magnolia,* normally produced as a small ornamental tree.

1 Drawing Sheet

Figure 1:
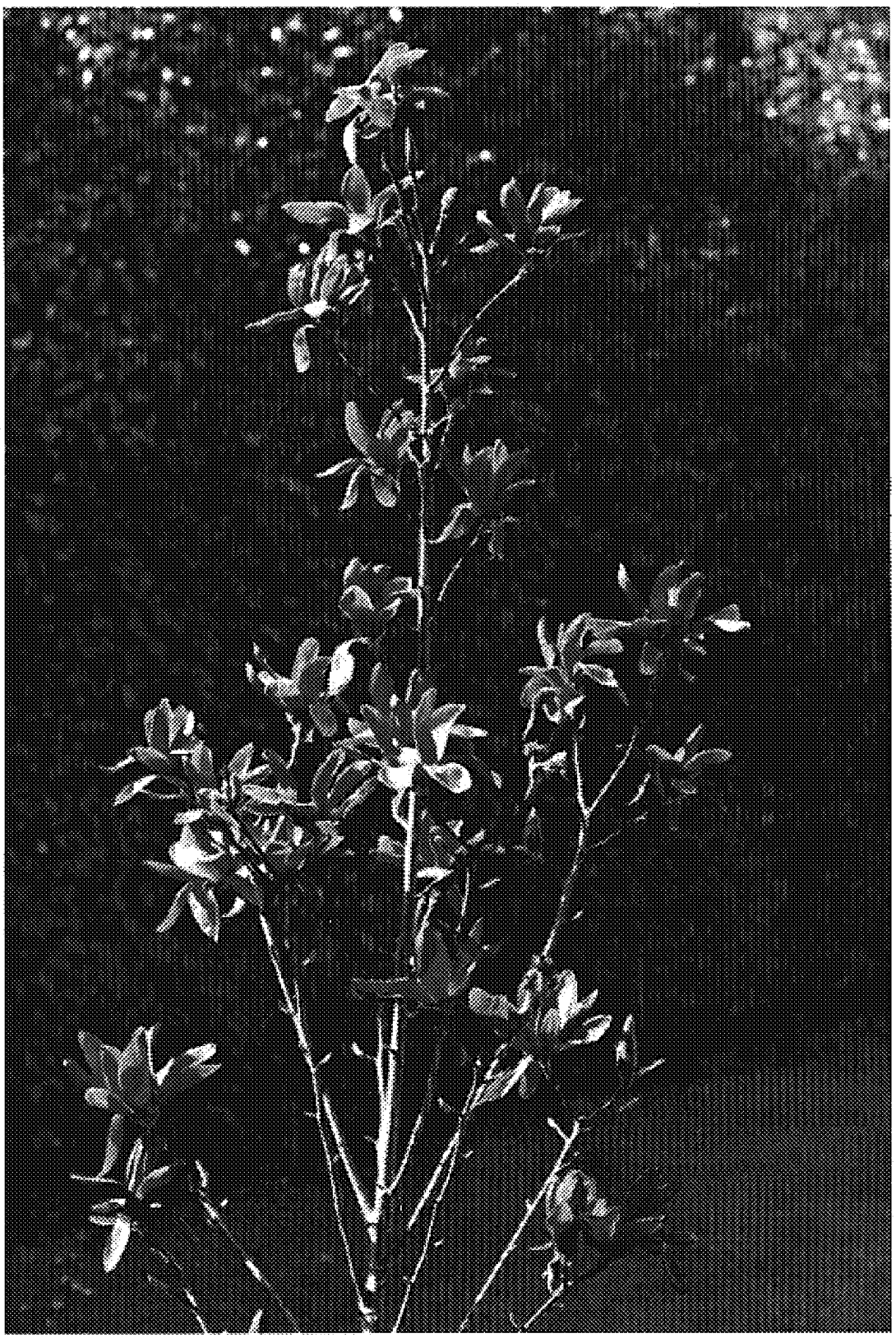

Latin name of the genus and species: *Magnolia hybrida.*
Variety denomination: 'JURmag4'.

BACKGROUND OF THE INVENTION

The new cultivar is a product of a planned breeding program. The new variety resulted from a crossing performed in 1993 in North Taranaki, Nth Is, New Zealand. The seed parent is the unpatented variety, *Magnolia lilliflora* 'Nigra'. The pollen parent is the unpatented variety *Magnolia* hybrid 'Vulcan.' The new variety was selected 2002, by the inventor, Mark Jury at North Taranaki, Nth Is, New Zealand in a group of approximately 15 seedlings.

Asexual reproduction of the new cultivar 'JURmag4' by vegetative cuttings was performed at a commercial nursery in New Zealand and has shown that the unique features of this cultivar are stable and reproduced true to type on successive generations.

SUMMARY OF THE INVENTION

The cultivar 'JURmag4' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'JURmag4' These characteristics in combination distinguish 'JURmag4' as a new and distinct *Magnolia* cultivar:

1. Upright, fastigiate habit.
2. Dark pink petals.
3. Controlled growth without pruning.
4. Star shaped flowers.
5. Profuse flowering.

PARENT COMPARISON

Plants of the new cultivar 'JURmag4' are similar to plants of the seed parent, *Magnolia lilliflora* 'Nigra' in most horticultural characteristics, however, plants of the new cultivar 'JURmag4' have larger flowers of a brighter, deeper color than the parent variety. Additionally, the new variety has a much more upright, fastigiated growth habit than the seed parent variety.

Plants of the new cultivar 'JURmag4' are similar to plants of the pollen parent, *Magnolia hyb.* 'Vulcan' in most horticultural characteristics, however, plants of the new cultivar 'JURmag4' have smaller flowers of a darker color than the parent variety. Additionally, the new variety has a much more upright, fastigiated growth habit and slower growing than the pollen parent variety.

The seed and pollen parent varieties are the best commercial comparison to the new variety 'JURmag4.'

BRIEF DESCRIPTION OF THE PHOTOGRAPH

The accompanying photograph in FIG. 1 illustrates in full color a typical plant of 'JURmag4' outdoors. Age of the plant photographed is approximately 12 years from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'JURmag4' plants grown outdoors in New Zealand. Growing conditions are similar to USDA zone 7. Measurements and numerical values represent averages of typical plant types.

Botanical classification: *Magnolia hybrida* cultivar 'JURmag4.'

PROPAGATION

Time to initiate roots: About 60 days at approximately 21° C.
Time to produce a rooted cutting: About 120 days at 21° C.
Root description: Typical *Magnolia* root, thick, coarse, and white.

PLANT

Growth habit: Fastigiated tree.
Age of plant described: 12 years.
In a container or in the ground: Ground.
Height: Approximately 6 meters.
Plant spread: Approximately 2 meters.
Growth rate: Approximately 12 to 16 years to reach 6 meters.
Branching characteristics: Normally a single trunk tree with lateral branches forming at acute angles, 15–30 degree, to the trunk.
Length of primary lateral branches: Approximately 20 cm.
Diameter of lateral branches: Approximately 1 cm.
Quantity of lateral branches: Numerous.
Branching arrangement: Sub-opposite.
Trunk:
*Diameter.*—Approximately 12 cm, after 12 years.
*Texture.*—Smooth.
*Color.*—Near RHS Greyed-Green 189B.

FOLIAGE

Leaf:
*Arrangement.*—Alternate.
*Quantity.*—Approximately 8 per main branch.
*Average length.*—Approximately 16 cm.
*Average width.*—Approximately 8 cm.
*Shape of blade.*—Ovate.
*Apex.*—Acuminate.
*Base.*—Cuneate.
*Margin.*—Entire.
*Texture of top surface.*—Smooth.
*Texture of bottom surface.*—Moderately pubescent.
*Pubescence.*—Moderate, present only on underside.
*Leaf internode length.*—Approximately 3 cm.
*Color.*—Young foliage upper side: Newest foliage Near RHS Red 53B mixed with Green 143A. Young foliage under side: Newest foliage Near RHS Red 53B mixed with Green 143A. Mature foliage upper side: Near RHS Green 137A. Mature foliage under side: Near RHS Green 143A.
*Venation.*—Type: Pinnate. Venation color upper side: Near RHS Green 137B. Venation color under side; Near RHS Green 143B.
*Petiole.*—Average Length: Approximately 1.5 cm. Color: Near RHS Green 141B. Diameter: Approximately 3 cm.

FLOWER

Natural flowering season: August through September, in the Southern hemisphere.
Begins flowering after how many years/months: 1 year from bud stage.
Inflorescence type and habit: Singly occurring star shaped, profuse flowering.
Rate of flower opening: Approximately 6 days from bud to fully opened flower.
Flower longevity on plant: 4 to 5 days, after fully opened.
Quantity of flowers: Profuse, hundreds per tree.
Inflorescence size:
*Diameter.*—Approximately 20 cm.
*Height.*—Approximately 20 cm.
Pedicel:
*Length.*—1 cm.
*Diameter.*—1 cm.
Petals:
*Petal/arrangement.*—Whorled, overlapping.
*Size.*—Length: 9.5 cm. Width: 3.5 cm.
*Margin.*—Entire.
*Apex.*—Rounded.
*Petal quantity.*—12.
*Texture.*—Smooth.
Color: Petals: When opening:
*Upper surface.*—Near RHS Red 53B.
*Lower surface.*—Near RHS Red 53A.
*Fully opened.*—Upper surface: Near RHS Red 53C. Lower surface: Near RHS Red 53A. Color Changes when aging: Maintains the same tone, becomes slightly lighter.
Bud:
*Shape.*—Ovate to Lanceolate.
*Length.*—Approximately 8 cm.
*Diameter.*—Approximately 3 cm.
*Color.*—Near RHS Red 53A.
Sepals/tepals:
*Shape.*—Lanceolate.
*Quantity.*—12.
*Length.*—Approximately 0.95 cm.
*Width.*—Approximately 0.35 cm.
*Margin.*—Entire.
*Texture.*—Smooth.
Fragrance: Almost none to slightly scented.

REPRODUCTIVE ORGANS

Pollen:
*Color.*—Near RHS Yellow 12A.
*Quantity.*—Not measured.
Pistil:
*Stigma.*—Color: Near RHS White 155D. Ovary color: Near RHS Red 53B.

OTHER CHARACTERISTICS

Seeds and fruits: The new cultivar does not set seed.
Disease/pest resistance: Neither resistance nor susceptibility to pathogens and pests common to *Magnolia* have been observed.
Temperature tolerance: The new variety is suitable for growing in USDA zones 3 through 8.

What is claimed is:

1. A new and distinct cultivar of *Magnolia* tree named 'JURmag4' as herein illustrated and described.

* * * * *